United States Patent
Li et al.

(10) Patent No.: US 6,906,069 B1
(45) Date of Patent: Jun. 14, 2005

(54) LXR MODULATORS

(75) Inventors: Leping Li, Burlingame, CA (US); Julio C. Medina, San Carlos, CA (US); Bei Shan, Redwood City, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/479,315

(22) Filed: Jan. 6, 2000

Related U.S. Application Data

(60) Provisional application No. 60/115,292, filed on Jan. 8, 1999.

(51) Int. Cl.[7] .................................................. A01N 43/58
(52) U.S. Cl. ........................ 514/247; 514/461; 514/277; 514/438; 514/439
(58) Field of Search ........................ 546/283.4; 514/336

(56) References Cited

U.S. PATENT DOCUMENTS

| | | | | |
|---|---|---|---|---|
| 4,204,002 A | | 5/1980 | Hubele | ........................ 424/309 |
| 5,439,915 A | * | 8/1995 | Commons et al. | ........... 514/292 |
| 6,090,853 A | * | 7/2000 | Wetterich et al. | ........... 514/623 |

FOREIGN PATENT DOCUMENTS

| | | | |
|---|---|---|---|
| DE | 25 15 113 | 10/1975 | ......... C07C/103/46 |
| DE | 26 25 227 | 12/1976 | ......... C07D/231/40 |
| DE | 26 25 242 | 12/1976 | ......... C07D/307/66 |
| DE | 44 37 999 A1 | 5/1996 | ......... C07C/233/23 |
| DE | 44 38 020 A1 | 5/1996 | ......... C07C/233/41 |
| EP | 0 012 428 A1 | 6/1980 | ......... C07C/125/08 |
| EP | 0 013 360 A2 | 7/1980 | ......... C07D/249/08 |
| EP | 0 019 745 A1 | 12/1980 | .......... A01N/37/22 |
| EP | 0 023 669 A1 | 2/1981 | ....... C07C/103/737 |
| JP | 6323822 | 2/1988 | |
| JP | 0756392 | 7/1995 | |
| JP | 07118215 | 7/1995 | |
| WO | WO 94/21611 | 9/1994 | ......... C07D/213/75 |
| WO | WO 97/31637 | 9/1997 | ......... A61K/31/495 |
| WO | WO 9735838 A1 | * 10/1997 | ......... C07C/233/58 |
| WO | WO 99/06382 | 2/1999 | ......... C07D/295/10 |
| WO | WO 99/40064 | 8/1999 | ......... C07C/311/46 |
| WO | WO 99/44987 | 9/1999 | ......... C07C/279/12 |
| WO | WO 00/26186 | 5/2000 | ......... C07D/207/14 |
| WO | WO 00/54759 | 9/2000 | .......... A61K/31/00 |

OTHER PUBLICATIONS

Athelstan L.J. Beckwith, etal: "Tandem Radical Translocation and Homolytic Aromatic Substitution: a Convenient and Efficient Route to Oxindoles" *J. Chem. Soc. Chem. Commun.*; pp. 977–978; (1995).

Sylvie Le Blanc, etal: "New Access to Sprianc β–Lactams" *Tetrahedron* Lett; 33(15) pp. 1993–1996 (1992).

Masazumi Ikeda, etal "Photochemistry of 2-(N-Acyl-N-alkylamino)cyclohex-2-enones: Formation of Spiro-β-lactams" *Chem. Pharm. Bull;* 34(12) pp 4997–5004 (1986).

Masazumi Ikeda, etal "Photochemical Synthesis of Spiro-β-lactams" *J. Chem. Soc. Chem. Commun*; pp 758–759 (1984).

* cited by examiner

*Primary Examiner*—James O. Wilson
*Assistant Examiner*—Jason H. Johnsen
(74) *Attorney, Agent, or Firm*—Townsend and Townsend and Crew LLP

(57) ABSTRACT

The invention provides compounds, compositions and methods for modulating the effects of LXRα in a cell. The compounds and compositions are useful both as diagnostic indicators of LXRα function and as pharmacologically active agents. The compounds and compositions find particular use in the treatment of disease states associated with cholesterol metabolism, particularly atherosclerosis and hypercholesterolemia.

24 Claims, No Drawings

LXR MODULATORS

CROSS REFERENCE TO RELATED APPLICATIONS

This application claims the benefit of U.S. Provisional Application Ser. No. 60/115,292, filed Jan. 8, 1999, the contents of which are incorporated herein by reference.

STATEMENT REGARDING FEDERALLY SPONSORED RESEARCH

The invention described herein was not made with the aid of any federally sponsored grants.

FIELD OF THE INVENTION

The present invention relates to compounds and methods useful for the modulation of LXR and to compositions which modulate the activity of LXR. In view of the activity of LXR in the control of cholesterol homeostasis, the compounds described herein are useful for lowering plasma cholesterol levels.

BACKGROUND

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). Excess accumulation of cholesterol in the arterial walls can result in athersclerosis which is characterized by plaque formation. The plaques inhibit blood flow and promote clot formation, and can ultimately cause heart attacks, stroke and claudication. Development of therapeutic agents for the treatment of atherosclerosis and other diseases associated with cholesterol metabolism has been focused on achieving a more complete understanding of the biochemical pathways involved. Most recently, liver X receptors (LXRs) were identified as key components in cholesterol homeostasis.

The LXRs were first identified as orphan members of the nuclear receptor superfamily whose ligands and functions were unknown. Two LXR proteins α and β are known to exist in mammals. The expression of LXRα is restricted, with the highest levels being found in the liver, and lower levels found in kidney, intestine, spleen, and adrenals. See, Willy, et al., *Genes Dev.* 9(9): 1033–45 (1995). LXRβ is rather ubiquitous, being found in nearly all tissues examined. Recent studies on the LXRs indicate that they are activated by certain naturally occurring, oxidized derivatives of cholesterol, including 22(R)-hydroxycholesterol, 24(S)-hydroxycholesterol, and 24,25(S)-epoxycholesterol. See, Lehmann, et al., *J. Biol. Chem.* 272(6):3137–3140 (1997). The expression pattern of LXRs and their oxysterol ligands provided the first hint that these receptors may play a role in cholesterol metabolism. See, Janowski, et al., *Nature* 383:728–731 (1996).

As noted above, cholesterol metabolism in mammals occurs via conversion into steroid hormones or bile acids. The role of LXRs in cholesterol homeostasis was first postulated to involve the pathway of bile acid synthesis, in which cholesterol 7α-hydroxylase (CYP7α) operates in a rate-limiting manner. Support for this proposal was provided when additional experiments found that the CYP7α promoter contained a functional LXR response element that could be activated by RXR/LXR heterodimers in an oxysterol- and retinoid-dependent manner.

Confirmation of LXR function as a transcriptional control point in cholesterol metabolism was made using knockout mice, particularly those lacking LXRα. See, Peet, et al., *Cell* 93:693–704 (1998). Mice lacking the receptor LXRα (e.g., knockout or (−/−) mice) lost their ability to respond normally to increases in dietary cholesterol and were unable to tolerate any cholesterol in excess of that synthesized de novo. LXRα (−/−) mice did not induce transcription of the gene encoding CYP7α when fed diets containing additional cholesterol. This resulted in an accumulation of large amounts of cholesterol in the livers of LXRα (−/−) mice, and impaired hepatic function. These results further established the role of LXRα as the essential regulatory component of cholesterol homeostasis. LXRα is also believed to be involved in fatty acid synthesis. Accordingly, regulation of LXRα (e.g., use of LXRα antagonists) could provide treatment for a variety of lipid disorders including obesity and diabetes.

In view of the importance of LXRs, and particularly LXRα to the delicate balance of cholesterol metabolism and fatty acid biosynthesis, we describe modulators of LXRs which are useful as therapeutic agents or diagnostic agents for the treatment of disorders associated with bile acid and cholesterol metabolism, including cholesterol gallstones, atherosclerosis, lipid storage diseases, obesity, and diabetes. The agents described herein are also useful for disease states associated with serum hypercholesterolemia, such as coronary heart disease.

SUMMARY OF THE INVENTION

In one aspect, the present invention provides compositions for modulation of LXRα function in a cell. The compositions typically comprise a pharmaceutically acceptable excipient and a compound having the formula:

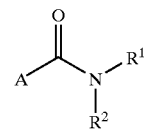

I or a pharmaceutically acceptable salt thereof, in which the letter A represents substituted or unsubstituted forms of $(C_5–C_{18})$alkyl or $(C_5–C_{18})$heteroalkyl; the symbol $R^1$ represents substituted or unsubstituted forms of $(C_3–C_{12})$alkyl, $(C_3–C_{12})$heteroalkyl, aryl, heteroaryl, aryl$(C_1–C_8)$alkyl, heteroaryl$(C_1–C_8)$alkyl, aryl$(C_2–C_8)$heteroalkyl or heteroaryl$(C_2–C_8)$heteroalkyl; and the symbol $R^2$ represents substituted or unsubstituted forms of aryl, heteroaryl, aryl$(C_1–C_8)$alkyl, heteroaryl$(C_1–C_8)$alkyl, aryl$(C_2–C_8)$heteroalkyl or heteroaryl$(C_2–C_8)$heteroalkyl. Optionally, $R^1$ and $R^2$ are combined with the nitrogen atom to which each is attached, to form a 5-, 6-, 7- or 8-membered ring. Preferred compositions are those in which the compound above binds to the ligand binding domain of LXRα with an affinity of at least 1 micromolar.

A number of the compounds used in the present compositions are novel. Accordingly, the present invention provides, in another aspect, compounds having the formula:

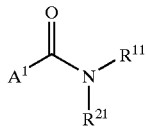

II or a pharmaceutically acceptable salt thereof, wherein the symbol $A^1$ represents substituted or unsubstituted forms of $(C_5-C_{12})_2)$monocycloalkyl, $(C_5-C_{12})$ heteromonocycloalkyl, $(C_8-C_{18})$bicycloalkyl, $(C_8-C_{18})$ tricycloalkyl, $(C_8-C_{18})$heterobicycloalkyl or $(C_8-C_{18})$ heterotricycloalkyl. The symbol $R^{11}$ represents substituted or unsubstituted forms of $(C_3-C_{12})$alkyl, aryl, aryl$(C_1-C_8)$ alkyl, aryl$(C_2-C_8)$heteroalkyl, $(C_3-C_{12})$heteroalkyl, heteroaryl, heteroaryl$(C_1-C_8)$alkyl or heteroaryl$(C_2-C_8)$ heteroalkyl. The symbol $R^{21}$ represents substituted or unsubstituted forms of an aryl, heteroaryl, aryl$(C_1-C_8)$alkyl, aryl$(C2-C_8)$heteroalkyl, heteroaryl$(C_1-C_8)$alkyl or heteroaryl$(C_2-C_8)$heteroalkyl group. Additionally, $R^{11}$ and $R^{21}$ can be combined with the nitrogen atom to which each is attached to form a five- to eight-membered ring, with the following provisos:

when $R^{21}$ is 2-pyridyl, $R^{11}$ is other than a substituted or unsubstituted 2-(1-piperazinyl)ethyl or (tetrahydro-2H-pyrido[3,4-b]indol-2-yl)ethyl group;

when $R^{21}$ is substituted or unsubstituted phenyl, $R^{11}$ and $R^{21}$ are not combined to form a ring with the attached nitrogen atom; and when $R^{21}$ is substituted or unsubstituted phenyl, $R^{11}$ is not allyl, 2-(acylamino)ethyl, or benzyloxycarbonyl.

In yet another aspect, the present invention provides methods for modulating LXRα in a cell by administering to or contacting the cell with a composition containing a compound of Formula I above.

In still another aspect, the present invention provides methods for treating LXRα-responsive diseases by administering to a subject in need of such treatment, a composition containing a compound of Formula 1. These methods are particularly useful for the treatment of pathology such as hypercholesterolemia, atherosclerosis, and hyperlipoproteinemia. In certain embodiments, the compound can be administered to the subject in combination with an additional hypercholesterolemic agent, for example, bile acid sequestrants, nicotinic acid, fibric acid derivatives or HMG CoA reductase inhibitors.

Certain compounds of the present invention are antiproliferative and can be used in compositions for treating diseases associated with abnormal cell proliferation (e.g., cancer). Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

DETAILED DESCRIPTION OF THE INVENTION

Definitions

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multi-radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1— and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkoxy," employed alone or in combination with other terms means, unless otherwise stated, an alkyl group, as defined above, connected to the remainder of the molecule via an oxygen atom, such as, for example, methoxy, ethoxy, 1-propoxy, 2-propoxy and the higher homologs and isomers.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. The terms "cycloalkyl" and "heterocycloalkyl" are also meant to include bicyclic, tricyclic and polycyclic versions thereof. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, bicyclo[2.2.1]heptyl, bicyclo[2.2.2]octyl, adamantyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a carbon atom or a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted (C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R' and R" are independently selected from hydrogen, (C$_1$–C$_8$)alkyl and heteroalkyl, unsubstituted aryl, (unsubstituted aryl)-(C$_1$–C$_4$) alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'- or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'- and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula 1. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

General

The present invention provides compositions, compounds and methods for modulating LXRα function in a cell. The compositions which are useful for this modulation will typically be those which contain an effective amount of an LXRα-modulating compound. In general, an effective amount of an LXRα-modulating compound is a concentration of the compound that will produce at 50 percent increase/decrease in LXRα activity in a cell-based reporter gene assay, or a biochemical peptide-sensor assay such as that described in co-pending application Ser. Nos. 08/975,614 (filed Nov. 21, 1997) and 09/163,713 (filed Sep. 30, 1998).

Embodiments of the Invention

Compositions

In one aspect, the present invention provides compositions for modulation of LXRα function in a cell. The compositions typically comprise a pharmaceutically acceptable excipient and a compound having the formula:

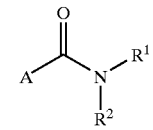

I or a pharmaceutically acceptable salt thereof, in which the letter A represents substituted or unsubstituted forms of $(C_5-C_{18})$alkyl or $(C_5-C_{18})$heteroalkyl. The symbol $R^1$ represents substituted or unsubstituted forms of $(C_3-C_{12})$alkyl, aryl, aryl$(C_1-C_8)$alkyl, aryl$(C_2-C_8)$heteroalkyl, $(C_3-C_2)$ heteroalkyl, heteroaryl, heteroaryl$(C_1-C_8)$alkyl or heteroaryl$(C_2-C_8)$heteroalkyl. The symbol $R^2$ represents substituted or unsubstituted forms of aryl, heteroaryl, aryl $(C_1-C_8)$alkyl, heteroaryl$(C_1-C_8)$alkyl, aryl$(C_2-C_8)$ heteroalkyl or heteroaryl$(C_2-C_8)$heteroalkyl. Optionally, $R^1$ and $R^2$ can be combined with the nitrogen atom to which each is attached to form a 5-, 6-, 7- or 8-membered ring which may have from 0 to 2 additional heteroatoms as ring members. Examples of such rings include pyrrolidine, piperidine, morpholine, piperazine and the like. Preferred compositions are those in which the compound above binds to the ligand binding domain of LXRα with an affinity of at least 1 micromolar.

In certain preferred embodiments, A represents a substituted or unsubstituted form of a $(C_5-C_{18})$cycloalkyl or a $(C_5-C_{18})$heterocycloalkyl group, more preferably a $(C_8-C_{18})$bicycloalkyl, $(C_8-C_{18})$tricycloalkyl, $(C_8-C_{18})$ heterobicycloalkyl or $(C_8-C_{18})$heterotricycloalkyl group. In particularly preferred embodiments, A represents a substituted or unsubstituted tricyclo[3.3.1.1$^{3,7}$]decanyl (or adamantyl), bicyclo[3.2.1]octanyl, bicyclo[5.2.0]nonanyl, bicyclo[4.3.2]undecanyl, tricyclo[2.2.1.0.1]heptanyl, tricyclo[5.3.1.1$^1$]dodecanyl, tricyclo[5.4.0.0$^{2,9}$]undecanyl, tricyclo[5.3.2.0$^{4,9}$]dodecanyl, tricyclo[4.4.1.1$^{1,5}$]dodecanyl or tricyclo[5.5.1.0$^{3,11}$]tridecanyl group. More preferably, A is a substituted or unsubstituted adamantyl group, most preferably an unsubstituted 1-adamantyl group.

Turning next to $R^1$, preferred embodiments are those in which $R^1$ is aryl$(C_1-C_8)$alkyl or heteroaryl$(C_1-C_8)$alkyl. More preferably, $R^1$ is branched heteroaryl$(C_2-C_8)$alkyl, for example, 1-(furan-2-yl)ethyl, 1-(pyridin-2-yl)ethyl, 1-(furan-2-yl)-2-propyl, 1-(2-pyridyl)-2-propyl, 1-(furanyl) isobutyl, 1-(3-pyridyl)isobutyl, 1-(pyridin-4-yl)ethyl, 1-(pyridin-4-yl)isobutyl, and the like. Most preferably, $R^1$ is 1-(furan-2-yl)ethyl or 1-(pyridin-2-yl)ethyl. In still other preferred embodiments, $R^1$ is a branched $(C_3-C_8)$alkyl, more preferably an isopropyl group. In yet other preferred embodiments, $R^1$ is a heteroaryl$(C_3-C_8)$alkenyl group. More preferably, $R^1$ is a 1-(3-furanyl)-3-butenyl group.

Returning to formula I above, the symbol $R^2$ is preferably a substituted or unsubstituted aryl or heteroaryl, more preferably a substituted or unsubstituted form of a pyridyl, phenyl, pyrazinyl, pyrimidinyl, pyridazinyl, thienyl, thiazolyl or furanyl group.

Still other preferred embodiments of the present compositions are those in which the compound of formula I has preferred combinations for A, $R^1$ and $R^2$. In one preferred group of combinations, A is adamantyl and $R^1$ is aryl $(C_1-C_8)$alkyl or heteroaryl$(C_1-C_8)$alkyl. In another preferred group of compounds, A is adamantyl, $R^1$ is aryl $(C_1-C_8)$alkyl or heteroaryl$(C_1-C_8)$alkyl, and $R^2$ is aryl or heteroaryl. In yet another preferred group of combinations, A is adamantyl, $R^1$ is branched heteroaryl$(C_2-C_8)$alkyl, and $R^2$ is aryl or heteroaryl. Still other preferred combinations are those in which A is adamantyl, $R^1$ is aryl$(C_1-C_8)$alkyl or heteroaryl$(C_1-C_8)$alkyl, and $R^2$ is pyridyl, phenyl, pyrazinyl, pyrimidinyl, pyridazinyl, thienyl, thiazolyl or furanyl.

Another group of preferred compounds for use in the present compositions are those in which A is substituted or unsubstituted adamantyl, $R^1$ is aryl$(C_3-C_8)$alkenyl or heteroaryl$(C_3-C_8)$alkenyl, and $R^2$ is a substituted or unsubstituted pyridyl or phenyl group. More preferably, the compounds are those in which A is unsubstituted 1-adamantyl, $R^1$ is phenyl$(C_3-C_8)$alkenyl or furanyl$(C_3-C_8)$alkenyl, and $R^2$ is a substituted or unsubstituted pyridyl or phenyl group. Most preferably, A is unsubstituted 1-adamantyl, $R^1$ is 1-(3-furanyl)-3-butenyl, and $R^2$ is a substituted or unsubstituted pyridyl or phenyl group. Preferred substituents for the phenyl or pyridyl group are small electron-withdrawing substituents, for example, halogen, halo$(C_1-C_3)$alkyl, nitro, cyano, and the like.

In another group of preferred compounds for use in the present compositions, A is substituted or unsubstituted adamantyl, $R^1$ is branched $(C_3-C_8)$alkyl, and $R^2$ is a substituted or unsubstituted pyridyl or phenyl group. More preferably, the compounds are those in which A is unsubstituted 1-adamantyl, $R^1$ is branched $(C_3-C_8)$alkyl, and $R^2$ is a substituted or unsubstituted pyridyl or phenyl group. Most preferably, A is unsubstituted 1-adamantyl, $R^1$ is isopropyl, and $R^2$ is a substituted or unsubstituted pyridyl or phenyl group. Preferred substituents for the phenyl or pyridyl group are small electron-withdrawing substituents, for example, halogen, halo$(C_1-C_3)$alkyl, nitro, cyano, and the like.

Compounds

A number of the compounds used in the present compositions are novel. Accordingly, the present invention provides, in another aspect, compounds having the formula:

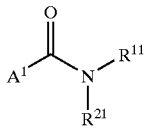

II or a pharmaceutically acceptable salt thereof, wherein the symbol $A^1$ represents substituted or unsubstituted forms of $(C_5-C_{12})$monocycloalkyl, $(C_5-C_{12})$heteromonocycloalkyl, $(C_8-C_{18})$bicycloalkyl, $(C_8-C_{18})$tricycloalkyl, $(C_8-C_{18})$heterobicycloalkyl or $(C_8-C_{18})$heterotricycloalkyl. The symbol $R^{11}$ represents substituted or unsubstituted forms of $(C_3-C_{12})$alkyl, aryl, aryl$(C_1-C_8)$alkyl, aryl$(C_2-C_8)$heteroalkyl, $(C_3-C_{12})$heteroalkyl, heteroaryl, heteroaryl $(C_1-C_8)$alkyl or heteroaryl$(C_2-C_8)$heteroalkyl. The symbol $R^{21}$ represents an aryl, heteroaryl, aryl$(C_1-C_8)$alkyl, heteroaryl$(C_1-C_8)$alkyl, aryl$(C_2-C_8)$heteroalkyl or heteroaryl$(C_2-C_8)$heteroalkyl group. Additionally, $R^{11}$ and $R^{21}$ can be combined with the nitrogen atom to which each is attached to form a five- to eight-membered ring, with the following provisos:

when $R^{21}$ is 2-pyridyl, $R^{11}$ is other than a substituted or unsubstituted 2-(1-piperazinyl)ethyl or (tetrahydro-2H-pyrido[3,4-b]indol-2-yl)ethyl group;

when $R^{21}$ is substituted or unsubstituted phenyl, $R^1$ and $R^{2'}$ are not combined to form a ring with the attached nitrogen atom; and when $R^{21}$ is substituted or unsubstituted phenyl, $R^{11}$ is not allyl, 2-(acylamino)ethyl, or benzyloxycarbonyl.

In formula II above, $A^1$ is preferably a substituted or unsubstituted form of $(C_8-C_{18})$bicycloalkyl, $(C_8-C_{18})$ tricycloalkyl, $(C_8-C_{18})$heterobicycloalkyl or $(C_8-C_{18})$ heterotricycloalkyl, more preferably, $(C_8-C_{18})$tricycloalkyl or $(C_8-C_{18})$heterotricycloalkyl. Still more preferably, $A^1$ is a substituted or unsubstituted form of $(C_8-C_{18})$tricycloalkyl, with substituted or unsubstituted adamantyl being most preferred.

Preferred groups for $R^{11}$ are aryl$(C_1-C_8)$alkyl and heteroaryl$(C—C_8)$alkyl. More preferably, $R^{11}$ is branched heteroaryl$(C_2-C_8)$alkyl, for example, 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl) isobutyl, 1-(pyridin-4-yl)ethyl, 1-(pyridin-4-yl)isobutyl, 1-(2-furanyl)-3-butenyl, 1-(3-furanyl)-3-butenyl and the like. Most preferably, $R^{11}$ is 1-(furan-2-yl)ethyl, 1-(3-furanyl)-3-butenyl or 1-(pyridin-2-yl)ethyl.

Preferred groups for $R^{21}$ include aryl or heteroaryl, more preferably substituted or unsubstituted forms of pyridyl, phenyl, pyrazinyl, pyrimidinyl, pyridazinyl, thienyl, thiazolyl or furanyl.

As with the compounds used in the compositions above, certain combinations of substituents represent particularly preferred embodiments of the invention. For example, when $A^1$ is adamantyl, $R^{11}$ is preferably aryl$(C_1-C_8)$alkyl or heteroaryl$(C_1-C_8)$alkyl, and $R^{21}$ is preferably aryl or heteroaryl. Still more preferred are those combinations in which $R^{11}$ is branched heteroaryl$(C_2-C_8)$alkyl, and $R^{2'}$ is aryl or heteroaryl. Still other preferred compounds are those in which $A^1$ is adamantyl, $R^{11}$ is aryl$(C_1-C_8)$alkyl or heteroaryl $(C_1-C_8)$alkyl, and $R^{21}$ is pyridyl, phenyl, pyrazinyl, pyrimidinyl, pyridazinyl, thienyl, thiazolyl or furanyl.

Still other preferred compounds are those in which $A^1$ is substituted or unsubstituted adamantyl, $R^{11}$ is aryl$(C_3-C_8)$ alkenyl or heteroaryl$(C_3-C_8)$alkenyl, and $R^{21}$ is a substituted or unsubstituted pyridyl or phenyl group. More preferably, the compounds are those in which $A^1$ is unsubstituted 1-adamantyl, $R^{11}$ is phenyl$(C_3-C_8)$alkenyl or furanyl$(C_3-C_8)$alkenyl, and $R^{21}$ is a substituted or unsubstituted pyridyl or phenyl group. Most preferably, $A^1$ is unsubstituted 1-adamantyl, $R^{11}$ is 1-(3-furanyl)-3-butenyl, and $R^{21}$ is a substituted or unsubstituted pyridyl or phenyl group. Preferred substituents for the phenyl or pyridyl group are small electron-withdrawing substituents, for example, halogen, halo$(C_1-C_3)$alkyl, nitro, cyano, and the like.

In another group of preferred compounds for use in the present compositions, $A^1$ is substituted or unsubstituted adamantyl, $R^{11}$ is branched $(C_3-C_8)$alkyl, and $R^{21}$ is a substituted or unsubstituted pyridyl or phenyl group. More preferably, the compounds are those in which $A^1$ is unsubstituted 1-adamantyl, $R^{11}$ is branched $(C_3-C_8)$alkyl, and $R^{21}$ is a substituted or unsubstituted pyridyl or phenyl group. Most preferably, $A^1$ is unsubstituted 1-adamantyl, $R^{11}$ is isopropyl, and $R^{2'}$ is a substituted or unsubstituted pyridyl or phenyl group. Preferred substituents for the phenyl or pyridyl group are small electron-withdrawing substituents, for example, halogen, halo$(C_1-C_3)$alkyl, nitro, cyano, and the like.

Methods

In yet another aspect, the present invention provides methods for modulating the action of LXRα in a cell. According to this method, the cell is contacted with a sufficient concentration of a composition containing a compound of formula I, above, for either an agonistic or antagonistic effect to be detected.

In still another aspect, the present invention provides methods for the treatment of pathology such as hypercholesterolemia, atherosclerosis, and hyperlipoproteinemia using pharmaceutical compositions containing compounds of the foregoing description of the general Formula I. Briefly, this aspect of the invention involves administering to a patient an effective formulation of one or more of the subject compositions. In other embodiments, the compound of Formula I can be administered in combination with other hypercholesterolemic agents (e.g., a bile acid sequestrant, nicotinic acid, fibric acid derivatives or HMG CoA reductase inhibitors), or in combination with other agents that affect cholesterol or lipid metabolism.

Preferred compounds and compositions for use in the present methods are those which have been described in the preceding sections.

Synthesis

Compounds of the present invention can be prepared using readily available starting materials or known intermediates. In general, the compounds are prepared from a carboxylic acid (or activated form thereof) of the formula A—$CO_2H$ and a secondary amine of the formula $R^1$—NH—$R^2$ using known coupling procedures. A number of monocyclic, bicyclic and tricyclic alkane carboxylic acids are commercially available, including, for example, 1-adamantanecarboxylic acid, 3-noradamantanecarboxylic acid, 5-norbornene-2-carboxylic acid, and 1-methyl-1-cyclohexanecarboxylic acid.

Amines which are useful in forming the compound and compositions of the present invention are also readily accessible either through commercial sources or via chemical synthesis. For example, an arylamine ($Ar^1$—$NH_2$) can be condensed with an aryl ketone (e.g., $CH_3C(O)Ar^2$) to yield an imine which can then be reduced to provide a suitable disubstituted amine (see Scheme 1). In some instances the intermediate imine can be converted to the amine in situ.

Scheme 1

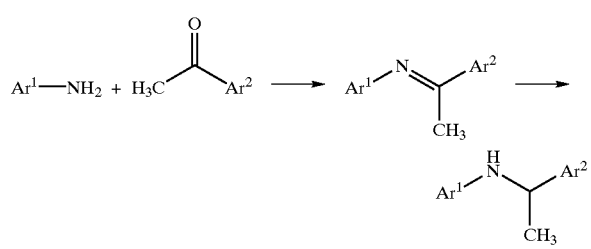

One of skill in the art will understand that the above reaction scheme can also be used with, for example, non-aromatic amines and aldehydes or other ketones. An alternative method to the reductive amination procedure outlined above is described in the Examples section below.

Regardless of the source or procedure used to obtain a suitable amine component, coupling of the amine to an appropriate carboxylic acid, carboxylic acid chloride, or activated ester is straightforward and can be accomplished using standard procedures.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3H$ (tritium) and $^{14}C$ (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

Analysis of Compounds

Representative compounds and compositions were demonstrated to have pharmacological activity in in vitro and cell culture assays, e.g., they are capable of specifically modulating a cellular physiology to reduce an associated pathology or provide or enhance a prophylaxis.

Certain preferred compounds and compositions are capable of specifically regulating LXRα. Compounds may be evaluated in vitro for their ability to activate LXRα receptor function using cell-based assays such as that described in Lehmann, et al. (*J. Biol. Chem.* 1997, 272(6), 3137–3140) or biochemical assays (see co-pending application Ser. Nos. 08/975,614 (filed Nov. 21, 1997) and 09/163,713 (filed Sep. 30, 1998)). Alternatively, the compounds and compositions can be evaluated for their ability to increase or decrease gene expression modulated by LXR, using western-blot analysis. Established animal models to evaluate hypocholesterolemic effects of compounds are known in the art. For example, compounds disclosed herein can be tested for their ability to lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med. Chem.* 1995, 38, 277). Still further, LXRα animal models (e.g., LXRα (+/−) and (−/−) mice) can be used for evaluation of the present compounds and compositions (see, for example, Peet, et al. *Cell* 1998, 93, 693–704).

Formulation and Administration of Compounds and Pharmaceutical Compositions

The invention provides methods of using the subject compounds and compositions to treat disease or provide medicinal prophylaxis, to activate LXR receptor function in a cell, to reduce blood cholesterol concentration in a host, to slow down and/or reduce the abnormal cellular proliferation including the growth of tumors, etc. These methods generally involve contacting the cell or cells with or administering to a host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic therapeutic or prophylactic agents, different from the subject compounds. In some instances, administration in conjunction with the subject compositions enhances the efficacy of such agents (i.e., there is a synergistic effect between the agents used in combination). Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). Abbreviations used in the examples below have their accepted meanings in the chemical literature. For example, THF (tetrahydrofuran), LDA (lithium diisopropylamide), MeCN (acetonitrile), and DMAP (4-dimethyaminopyridine).

The compounds provided in Examples 1–8 were synthesized using the general scheme provided below (Scheme 2) for the preparation of 1-(2-furanyl)-ethylamine derivatives.

The compounds provided in Examples 9 and 10 were prepared using similar methods. Suitable alteration of the various components in Scheme 2, including the secondary mesylate (ii), the amine used to displace the mesylate (to form iii), or the acyl chloride (used in the final step) provide entry into a wide variety of compounds of the present invention. As provided in the scheme, a suitable alcohol (i), preferably a primary or secondary alcohol, can be converted to a leaving group (e.g., a mesylate ester with the addition of methanesulfonylchloride) to provide an intermediate such as ii. Treatment of ii with a primary amine such as R—NH$_2$ provides the amine derivative iii. Subsequent acylation of the secondary amine functional group present in iii with acylating agents (R$^1$—COCl) provides the target compounds iv.

Scheme 2

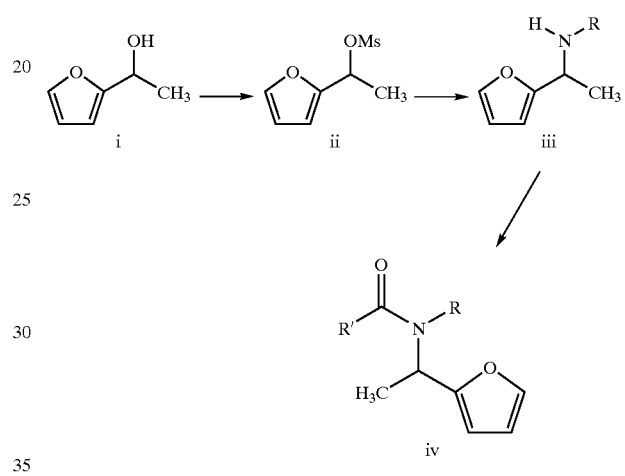

Example 1

This Example Illustrates the Preparation of Compound 1.

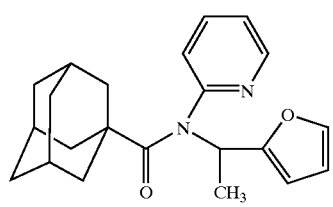

1

1.1 Preparation of Intermediate 2-(1-(furan-2-yl)ethyl) aminopyridine (1.1)

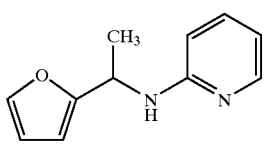

1.1

(±)-1-(2-furyl)ethanol (10.8 g, 95.4 mmol) was dissolved in THF (264 mL) under N$_2$ at ambient temperature. To the mixture was added LDA (52.5 mL of a 2.0 M solution in heptane/THF, 105 mmol, from Aldrich Chemical Co.) dropwise at −45° C. (dry ice/MeCN bath) over a period of 12 min. The mixture was stirred at −45° C. for 2 hours.

Methanesulfonyl chloride (9.0 mL, 115 mmol) was added dropwise at −45° C. for 10 min. The mixture was stirred at −45° C. for 2 h, then a solution of 2-aminopyridine (15.7 g, 167 mmol) in THF (367 mmol) was added dropwise at 45° C. over 15 min. The resulting mixture was quenched with water, extracted with CHCl₃, and the organic layer was washed with brine and dried over MgSO₄. The solvent was removed by evaporation and the crude product was purified by column chromatography on silica gel to afford the title compound as an oil in 51.8% yield.

$^1$H-NMR (CDCl₃ 400 MHz) δ 8.1 (d, J=4.76 Hz, 1H), 7.44–7.34 (m, 2H), 6.59 (dd, J=5.12, 7.2 Hz, 1H), 6.40 (d, J=8 Hz, 1H), 6.30 (m, 1H), 6.17 (d, J=3.16 Hz, 1H), 5.04 (m, 1H), 4.85 (m, 1H), 1.58 (d, J=6.64 Hz, 3H).

1.2 Preparation of Compound 1

To (1-furan-2-yl-ethyl)-pyridin-2-yl-amine (2.82 g, 15.0 mmol) in pyridine (24.2 mL) was added in one portion 1-adamantanecarbonyl chloride (9.40 g, 44.9 mmol) and DMAP (92 mg, 0.753 mmol) under N₂ at ambient temperature. The reaction mixture was heated to reflux for 1.5 h, then allowed to cool, quenched with H₂O, and extracted with CHCl₃. The organic layer was washed with brine and dried over MgSO₄. The solvent was evaporated and the crude product was purified by recrystallizing from ethyl acetate/hexanes to afford 3.67 g of title compound.

$^1$H-NMR (CDCl₃, 400 MHz) δ 8.49 (m, 1H), 6.57 (d, J=7.96 Hz, 1H), 6.22 (d, J=1.89 Hz, 1H), 6.09 (m, 1H), 5.98 (m, 1H), 1.95–1.40 (m, 18H).

Example 2

This Example Illustrates the Preparation of Compound 2.

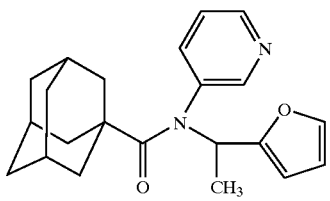

2

The title compound was prepared in a manner analogous to that described for the compound of Example 1.

$^1$H-NMR (CDCl₃, 400 MHz): δ 8.52 (d, J=4.4 Hz, 1H), 8.10 (br s, 1H), 7.35 (d, J=1.8 Hz, 1H), 7.20 (m, 1H), 7.05 (m, 1H), 6.22 (m, 2H), 5.93 (m, 1H), 1.84 (m, 2H), 1.72 (m, 6H), 1.56 (m, 3H), 1.45 (m, 3H), 1.34 (d, J=7 Hz, 3H).

Example 3

This Example Illustrates the Preparation of Compound 3.

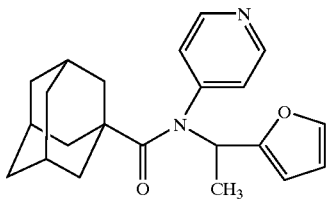

3

The title compound was prepared in a manner analogous to that described for the compound of Example 1.

$^1$H-NMR (CDCl₃, 400 MHz) δ 8.52 (d, J=2 Hz, 2H), 7.37 (s, 1H), 6.15 (m, 1H), 5.95 (d, J=3.28 Hz, 1H), 1.87–1.33 (m, 18H).

Example 4

This Example Illustrates the Preparation of Compound 4.

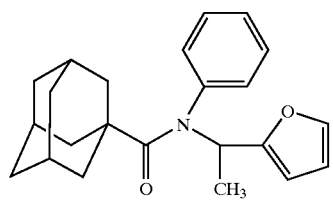

4

The title compound was prepared in a manner analogous to that described for the compound of Example 1.

$^1$H-NMR (CDCl₃, 400 Mhz) δ 7.34–7.20 (m, 5H), 6.8 (br s, 1H), 6.20 (m, 2H), 5.89 (m, 1H), 1.82–1.30 (m, 18H).

Example 5

This Example Illustrates the Preparation of Compound 5.

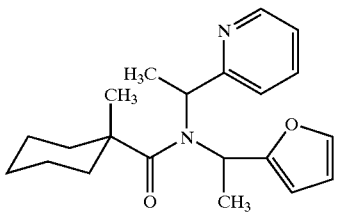

5

The title compound was prepared in a manner analogous to that described for the compound of Example 1. $^1$H-NMR (CDCl₃, 400 MHz) δ 8.49 (m, 1H), 7.52 (m, 1H), 7.35 (m, 1H), 7.20 (m, 1H), 6.57 (m, 1H) 6.23 (m, 1H), 6.15 (m, 1H), 6.00 (m, 1H), 1.90–0.80 (m, 16H).

Example 6

This Example Illustrates the Preparation of Compound 6.

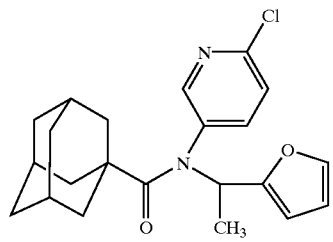

6

The title compound was prepared using methods outlined above.

$^1$H NMR (CDCl₃) δ 7.81 (broad s, 1H), 7.36 (s, 1H), 7.21 (d, J=8.4 Hz, 1H), 6.95 (broad s, 1H), 6.21 (m, 2H), 5.95 (m, 1H), 1.88 (m, 3H), 1.70 (m, 6H), 1.60 (d, J=12 Hz, 3H), 1.48

(d, J=12 Hz, 3H), 1.33 (d, J=7 Hz, 3H). MS (ES+): 385 (M+H, 100). Anal. Calcd. for $C_{22}H_{25}ClN_2O_2$: C, 68.65; H, 6.55; N, 7.28; Cl, 9.21. Found: C, 68.37; H, 6.56; N, 7.18; Cl, 9.46.

Example 7

This Example Illustrates the Preparation of Compound 7.

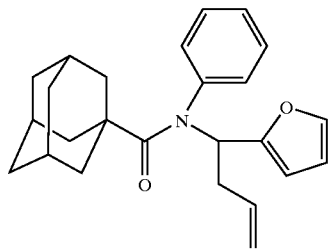

Step 7a

To a stirred solution of sodium docecylsulfate (12 mL, 35 mM in water) and scandium trifluoromethanesulfonate [Sc (OTf)$_3$, 214 mg] were added aniline (0.19 mL, 2.06 mmol), allyltributylstannane (0.94 mL, 3.01 mmol), and 2-furaldehyde (0.215 mL, 2.59 mmol) successively, and the mixture was stirred at room temperature. After 24 h, the mixture was diluted with water and ethyl acetate. After separation of layers, the organic layer was washed with saturated NaHCO$_3$ twice, dried over MgSO$_4$, filtered, ad concentrated. The crude product was purified by flash chromatography on silica gel eluted with hexane/ethyl acetate (20:1) to give 0.360 g of the desired homoallylic amine in 81.9% yield.

$^1$H NMR (CDCl$_3$) δ7.35 (s, 1H), 7.15 (t, J=6.8 Hz, 2H), 6.72 (t, J=6.8 Ha, 1H), 6.61 (d, J=6.8 HZ, 2H), 6.30 (d, J=1.8 Hz, 1H), 6.18 (d, J=1.8 Hz, 1H), 5.75 (m, 1H), 5.18 (d, J=18 Hz, 1H), 5.12 (d, J=10 Hz, 1H), 4.55 (m, 1H), 4.0 (bs, 1H), 2.66 (m, 1H).

Step 7b.

The mixture of 1-adamantanecarbonyl chloride (293 mg, 1.48 mmol), the above aniline (158 g, 0.74 mmol), 4-dimethylaminopyridine (DMAP, 30 mg, 0.25 mmol) in pyridine (2 mL) was heated at 90° C. for 3 days. The reaction mixture was diluted with ethyl acetate, washed with 1 N HCl (2×) and brine. The organic layer was dried over MgSO$_4$, filtered and stripped. The crude product was purified by flash chromatography on silica gel eluted with hexane/ethyl acetate (20:1) to give 80 mg of the title compound in 28.8% yield (along with recovered starting aniline).

$^1$H NMR (CD$_3$OD) δ 7.44 (s, 1H), 7.35 (m, 2H), 6.90 (m, 2H), 6.25 (d, J=4.8 Hz, 1H), 6.17 (t, J=7.7 Hz, 2H), 5.99 (d, J=4.8 Hz, 1H), 5.83 (m, 1H), 5.18 (d, J=18 Hz, 1H), 5.06 (d, J=12 Hz, 1H), 2.50 (t, J=4.8 Hz, 2H), 1.79 (bs, 3H), 1.75 (d, J=12 Hz, 3H), 1.68 (d, J=12 Hz, 3H), 1.52 (d, J=12 Hz, 3H), 1.43 (d, J=12 Hz, 3H). MS (ES+): 376 (M+H, 100). Anal. Calcd. for $C_{25}H_{29}NO_2$: C, 79.96; H, 7.78; N, 3.73. Found: C, 79.79; H, 7.86; N, 3.62.

Example 8

This Example Illustrates the Preparation of Compound 8.

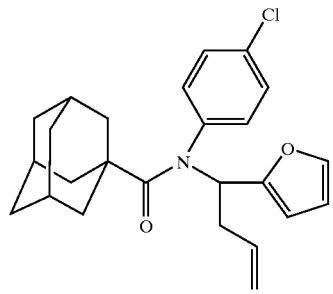

Step 8a:

Following the procedures described for Example 7 and substituting 4-chloroaniline for aniline, in Step 7a, the corresponding N-4-chlorophenylhomoallylamine was obtained, 0.448 g, 90.0%.

$^1$H NMR (CDCl$_3$) δ 7.34 (s, 1H), 7.08 (d, J=6.8 Hz, 2H), 6.52 (d, J=6.8 Hz, 2H), 6.29 (d, J=3.2 Hz, 1H), 6.13 (d, J=3.2 Hz, 1H), 5.75 (m, 1H), 5.18 (d, J=18 Hz, 1H), 5.13 (d, J=9.2 Hz, 1H), 4.50 (m, 1H), 3.99 (bs, 1H), 2.64 (m, 2H).

Step 8b:

Following conditions described in Step 7b and substituting the corresponding aniline with the 4-chlorosubstituted aniline from Step 8a, the title compound was obtained.

$^1$H NMR (CDCl$_3$) δ 7.30 (s, 1H), 7.00–7.30 (m, 4H), 6.21 (d, J=3.3 Hz, 1H), 6.20 (t, J=4.8 Hz, 1H), 5.95 (d, J=3.3 Hz, 1H), 5.78 (m, 1H), 5.13 (d, J=18 Hz, 1H), 5.08 (d, J=12 Hz, 1H), 2.44 (m, 2H), 1.83 (bs, 3H), 1.73 (d, J=12 Hz, 3H), 1.69 (d, J=12 Hz, 3H), 1.56 (d, J=12 Hz, 3H), 1.46 (d, J=12 Hz, 3H). MS (ES+): 410 (M+H, 100). Anal. Calcd. for $C_{25}H_{28}ClNO_2$: C, 73.25; H, 6.88; N, 3.42. Found: C, 73.27; H, 6.94; N, 3.34.

Example 9

This Example Illustrates the Preparation of Compound 9.

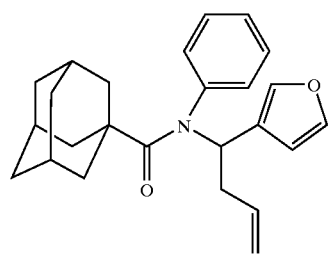

Step 9a:

Following the procedures described for Example 7 and substituting 3-furaldehyde for 2-furaldehyde in Step 7a, the corresponding 3-furylhomoallylamine was obtained, 0.32 g, 66.0% yield.

$^1$H NMR (CDCl$_3$) δ 7.35 (bs, 1H), 7.32 (s, 1H), 7.04 (t, J=7.2 Hz, 2H), 6.70 (t, J=7.2 Hz, 1H), 6.60 (d, J=7.2 Hz, 2H), 6.36 (s, 1H), 5.80 (m, 1H), 5.16 (d, J=16 Hz, 1H), 5.12

(d, J=12 Hz, 1H), 4.48 (m, 1H), 3.90 (bs, 1H), 2.52 (m, 2H). MS (ES+): 214 (M+H, 100).

Step 9b:

Following conditions described in Step 7b and substituting the corresponding aniline with the aniline from Step 9a, the title compound was obtained in 28.3% yield.

$^1$H NMR (CDCl$_3$) δ 7.25–7.35 (m, 6H), 7.09 (s, 1H), 6.13 (s, 1H), 6.01 (t, J=6.0 Hz, 1H), 5.80 (m, 10H), 5.11 (d, J=18 Hz, 1H), 5.05 (d, J=12 Hz, 1H), 2.51 (m, 1H), 2.35 (m, 1H), 1.79 (bs, 3H), 1.68 (bs, 6H), 1.54 (d, J=12 Hz, 3H), 1.44 (d, J=12 Hz, 3H). MS (ES+): 376 (M+H, 100). Anal. Calcd. for C$_{25}$H$_{29}$NO$_2$: C, 79.96; H, 7.78; N, 3.73. Found: C, 79.89; H, 7.82; N, 3.72.

Example 10

This Example Illustrates the Preparation of Compound 10.

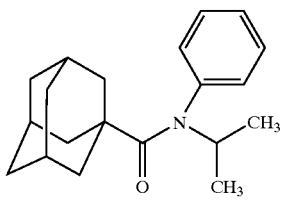

Following conditions described in Step 7b and substituting the aniline with isopropylamine, the title compound was obtained in 40% yield.

$^1$H NMR (CDCl$_3$) δ 7.35 (m, 3H), 7.11 (m, 2H), 4.92 (m, 1H), 1.79 (bs, 3H), 1.68 (bs, 6H), 1.53 (d, J=12 Hz, 3H), 1.48 (d, J=12 Hz, 3H), 0.98 (d, J=6.8 Hz, 6H). MS (ES+): 298 (M+H), 100.

Example 11

In order to identify agonists for LXRα, a cell-based high throughput screen was developed. Briefly, a DNA-binding domain of the nonreceptor transcription factor GAL4 was fused to the putative ligand-binding domain of LXRα. The resulting construct was introduced into 293 cells, together with an UAS-containing luciferase reporter construct. The transfected cells were then treated with the compounds and luciferase activity was measured. Individual compounds were evaluated relative to a control (no additional compound) at a concentration of 10 μM. Relative luciferase activity is provided below for five of the compounds described in the Examples above (luciferase activity of the control was assigned a value of 1).

| Example | Relative Activity |
|---|---|
| Example 1 | 4 |
| Example 2 | 5 |
| Example 3 | ≧10 |
| Example 4 | 3 |
| Example 5 | ≧10 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising a pharmaceutically acceptable excipient and a compound having the formula:

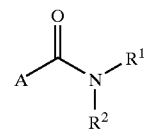

or a pharmaceutically acceptable salt thereof, wherein
A is adamantyl;
R$^1$ is a member selected from the group consisting of heteroaryl heteroaryl (C$_1$–C$_8$)alkyl; and
R$^2$ is heteroaryl when R$^1$ is heteroaryl and is heteroaryl (C$_1$–C$_8$)alkyl when R$^1$ is heteroaryl(C$_1$–C$_8$)alkyl.

2. A composition in accordance with claim 1, wherein R$^1$ is selected from the group consisting of 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, 1-(2-furanyl)-3-butenyl, and 1-(3-furanyl)-3-butenyl.

3. A composition in accordance with claim 2, wherein R$^1$ is selected from the group consisting of 1-(furan-2-yl)ethyl, 1-(3-furanyl)-3-butenyl and 1-(pyridin-2-yl)ethyl.

4. A composition in accordance with claim 1, wherein R$^2$ is heteroaryl.

5. A composition comprising a pharmaceutically acceptable excipient and a compound having the formula:

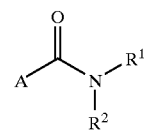

or a pharmaceutically acceptable salt thereof, wherein A is adamantyl, R$^1$ is selected from the group consisting of 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, 1-(2-furanyl)-3-butenyl and 1-(3-furanyl)-3-butenyl; and R$^2$ is selected from the group consisting of heteroaryl(C$_1$–C$_8$)alkyl and heteroaryl.

6. A composition in accordance with claim 5, wherein R$^1$ is 1-(2-furanyl)-3-butenyl or and 1-(3-furanyl)-3-butenyl and R$^2$ is pyridyl.

7. A composition in accordance with claim 5, wherein R$^1$ is selected from the group consisting of 1-(furan-2-yl)ethyl, 1-(3-furanyl)-3-butenyl and 1-(pyridin-2-yl)ethyl and R$^2$ is heteroaryl.

8. A composition in accordance with claim 1, wherein R$^2$ is selected from the group consisting of pyridyl, pyrazinyl, pyrimidinyl, pyridazinyl, thienyl, thiazolyl and furanyl.

9. A compound having the formula:

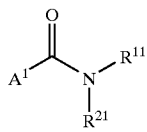

or a pharmaceutically acceptable salt thereof, wherein
A$^1$ is adamantyl;
R$^{11}$ is a member selected from the group consisting of heteroaryl heteroaryl (C$_1$–C$_8$)alkyl; and
R$^{21}$ is heteroaryl when R$^1$ is heteroaryl and is heteroaryl (C$_1$–C$_8$)alkyl when R$^1$ is heteroaryl(C$_1$–C$_8$)alkyl.

10. A compound in accordance with claim 9, wherein R$^{11}$ is selected from the group consisting of 1-(furan-2-yl)ethyl, 1-(pyridin-2-yl)ethyl, 1-(furan-2-yl-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, 1-(2-furanyl)-3-butenyl, and 1-(3-furanyl)-3-butenyl.

11. A compound of claim 9, wherein R$^{11}$ is selected from the group consisting of 1-(furan-2-yl)ethyl, 1-(pyridin-2-yl)ethyl and 1-(3-furanyl)-3-butenyl.

12. A compound in accordance with claim 9, wherein R$^{21}$ is heteroaryl.

13. A compound having the formula:

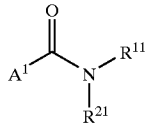

or a pharmaceutically acceptable salt thereof, wherein A$^1$ is adamantyl, R$^{11}$ is selected from the group consisting of 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, 1-(2-furanyl)-3-butenyl, and 1-(3-furanyl)-3-butenyl and R$^{21}$ is selected from the group consisting of heteroaryl(C$_1$–C$_8$)alkyl and heteroaryl.

14. A compound in accordance with claim 13, wherein R$^{11}$ is selected from the group consisting of 1-(2-furanyl)-3-butenyl and 1-(3-furanyl)-3-butenyl and R$^{21}$ is pyridyl.

15. A compound in accordance with claim 13, wherein R$^{11}$ is selected from the group consisting of 1-(furan-2-yl)ethyl, 1-(pyridin-2-yl)ethyl and 1-(3-furanyl)-3-butenyl and R$^{21}$ is heteroaryl.

16. A compound in accordance with claim 13, wherein R$^{11}$ is selected from the group consisting of 1-(furan-2-yl)ethyl, 1-(pyridin-2-yl)ethyl and 1-(3-furanyl)-3-butenyl and R$^{21}$ is selected from the group consisting of pyridyl, pyrazinyl, pyrimidinyl, pyridazinyl, thienyl, thiazolyl and furanyl.

17. A composition in accordance with claim 5, wherein R$^1$ is selected from the group consisting of 1-(furan-2-yl)ethyl, 1-(3-furanyl)-3-butenyl and 1-(pyridin-2-yl)ethyl.

18. A composition in accordance with claim 5, wherein R$^2$ is heteroaryl.

19. A composition in accordance with claim 1, wherein R$^2$ is pyridyl.

20. A composition in accordance with claim 5, wherein R$^2$ is selected from the group consisting of pyridyl, pyrazinyl, pyrimidinyl, pyridazinyl, thienyl, thiazolyl and furanyl.

21. A compound in accordance with claim 13, wherein R$^{11}$ is selected from the group consisting of 1-(furan-2-yl)ethyl and 1-(pyridin-2-yl)ethyl and 1-(3-furanyl)-3-butenyl.

22. A compound in accordance with claim 13, wherein R$^{21}$ is heteroaryl.

23. A compound in accordance with claim 9, wherein R$^{21}$ is selected from the group consisting of pyridyl, pyrazinyl, pyrimidinyl, pyridazinyl, thienyl, thiazolyl and furanyl.

24. A compound in accordance with claim 9, wherein R$^{21}$ is pyridyl.

* * * * *